United States Patent [19]

Attia et al.

[11] Patent Number: 4,775,627

[45] Date of Patent: Oct. 4, 1988

[54] COAL DESULFURIZATION USING BACTERIA ADAPTATION AND BACTERIAL MODIFICATION OF PYRITE SURFACES

[75] Inventors: Yosry A. Attia, Columbus, Ohio; Mohamed A. Elzeky, Victoria, Egypt

[73] Assignee: The Ohio State University, a branch of the State Government, Columbus, Ohio

[21] Appl. No.: 854,509

[22] Filed: Apr. 22, 1986

[51] Int. Cl.⁴ .............................................. C12P 1/04
[52] U.S. Cl. .................................. 435/262; 435/267; 435/282
[58] Field of Search ........................ 435/267, 262, 282

[56] References Cited

U.S. PATENT DOCUMENTS 4,206,288 6/1980 Detz et al. .
4,456,688 6/1984 Dugan et al. .
4,552,652 11/1985 Attia et al. .

OTHER PUBLICATIONS

Kempton et al.—Chem. Abst., vol. 92 (1980) p. 200695p.
Dutkiewicz et al.—Chem. Abst., vol. 90 (1979) p. 57612p.
Recent Progress in Biohydrometallurgy, Rossi and Torma, 1983.

Primary Examiner—Sam Rosen
Attorney, Agent, or Firm—Frank H. Foster

[57] ABSTRACT

The invention relates to the desulfurization of high sulfur coal, and specifically to the removal of pyrite from high sulfur coal via separation processes based on relative hydrophobicity. The surfaces of the pyrite particles are modified so as to be more hydrophilic by pre-conditioning of the coal with a culture of thiophilic bacteria such as *Thiobacillus ferroxidans*, and the coal is then subjected to the separation process. The bacterial culture is preadapted to pyrite and to the pyrite surface modification step conditions for a period of several weeks which allows the commercial preconditioning step to be accomplished in less than one hour and typically in five to fifteen minutes.

25 Claims, 6 Drawing Sheets

EFFECT OF FLOTATION REAGENTS DOSAGE
(DATA FROM TABLES 1 AND 2)

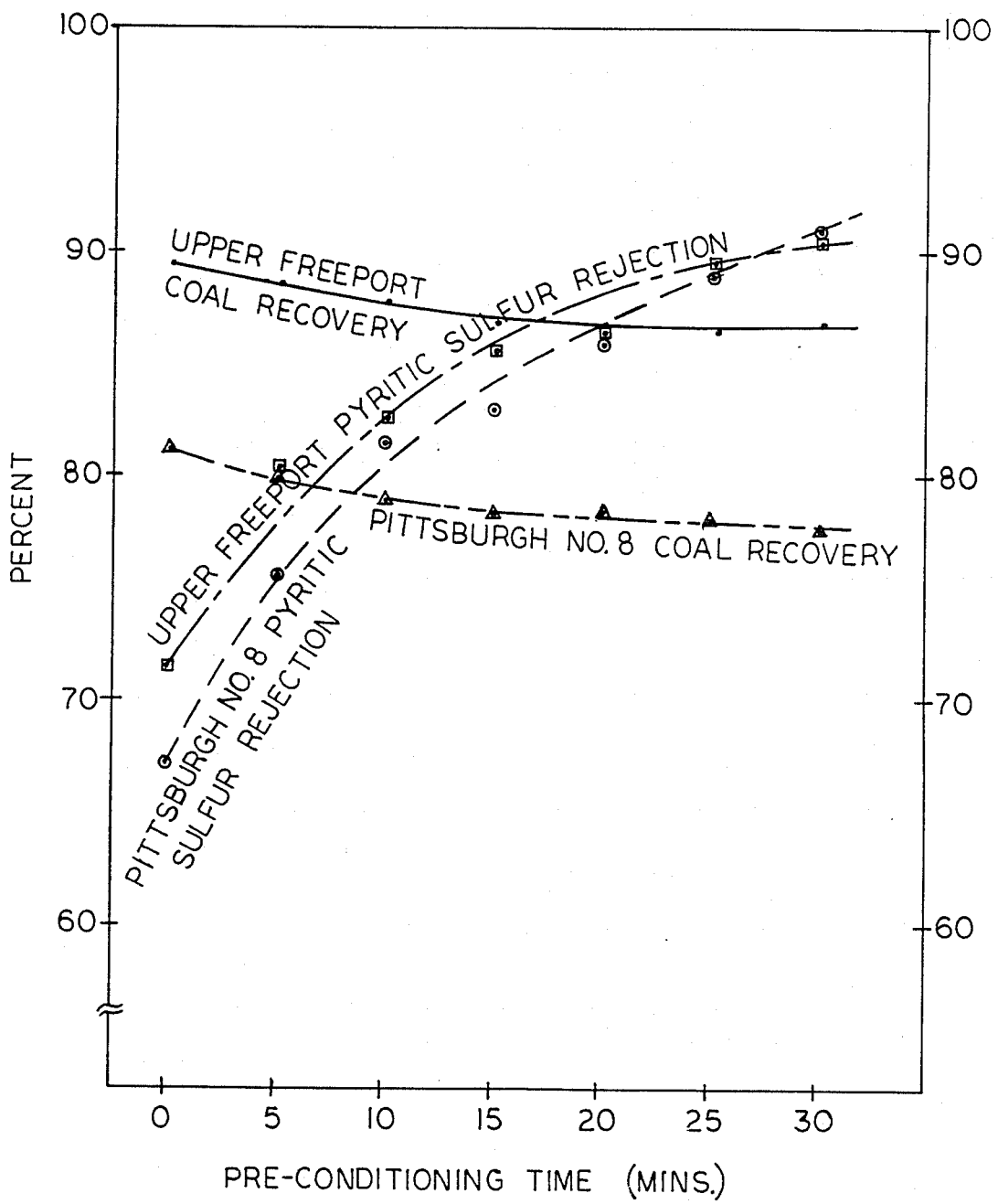

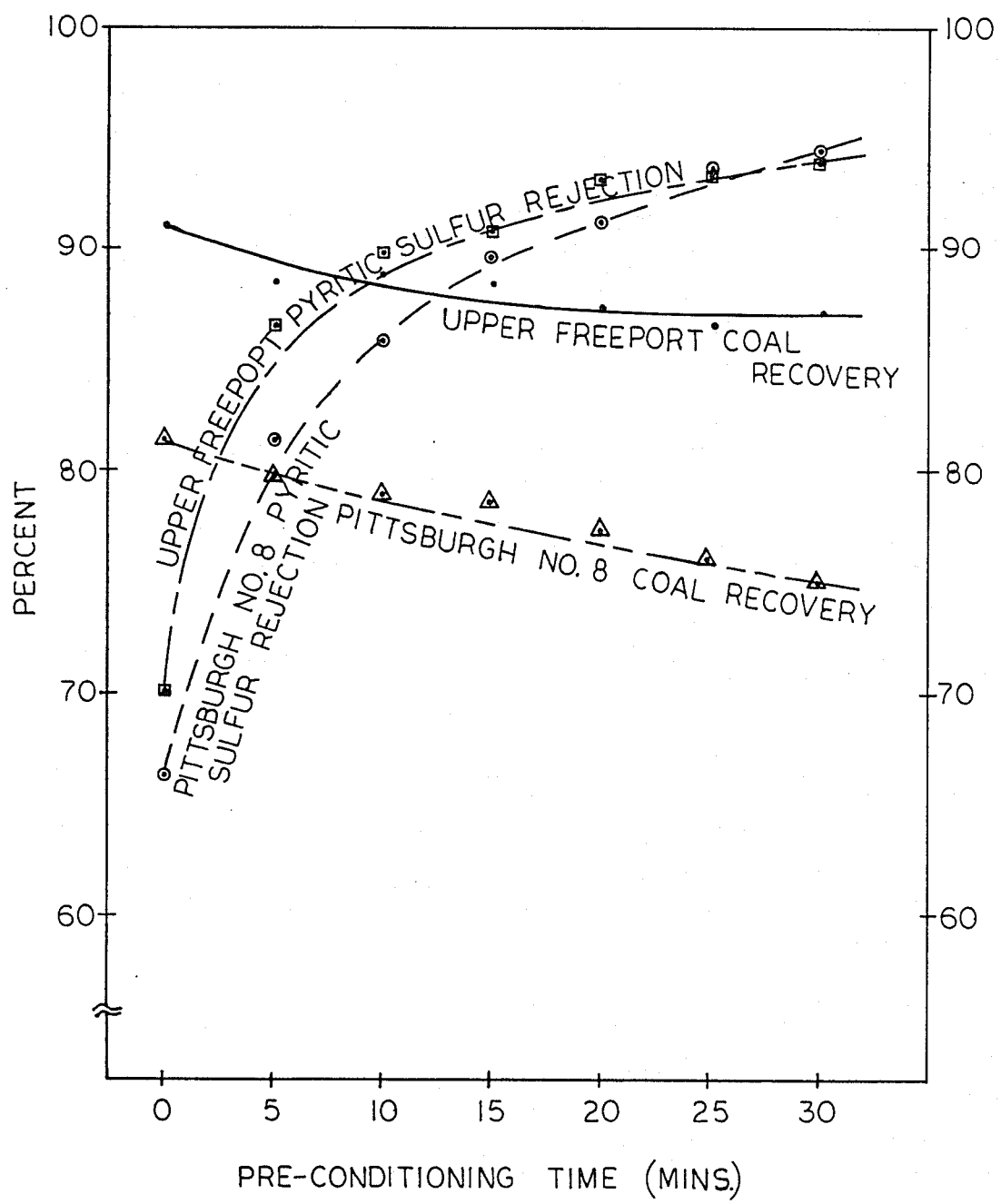

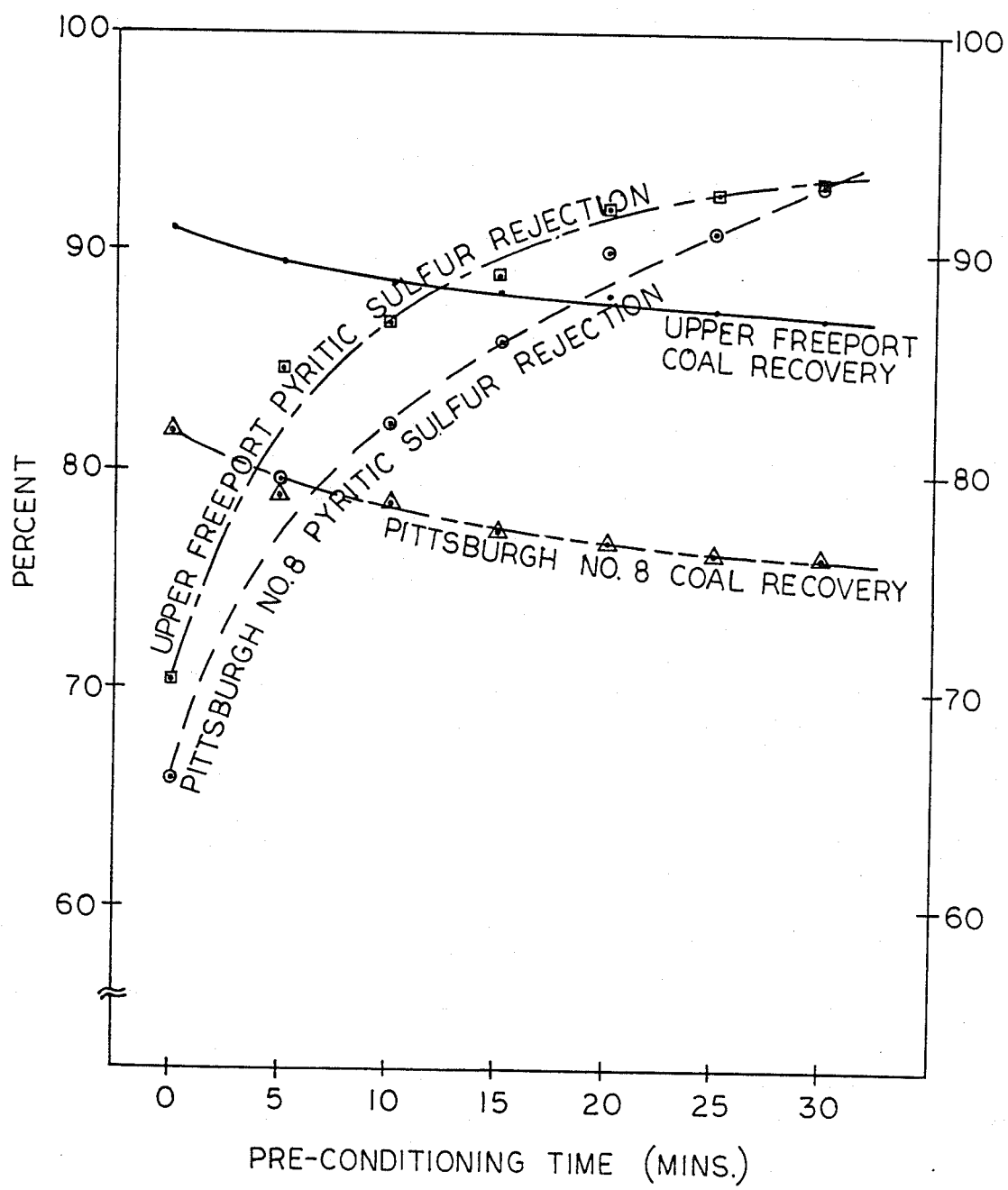

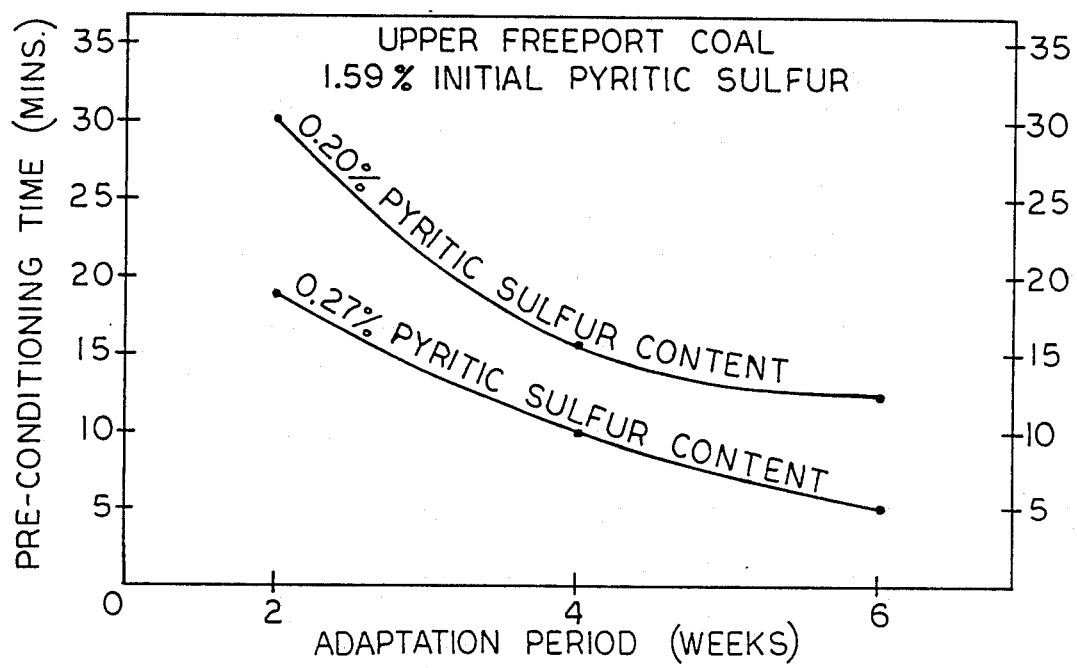
FIG. 6 EFFECT OF ADAPTATION PERIOD ON THE BACTERIAL PRE-CONDITIONING TIME IN THE FLOTATION OF UPPER FREEPORT COAL
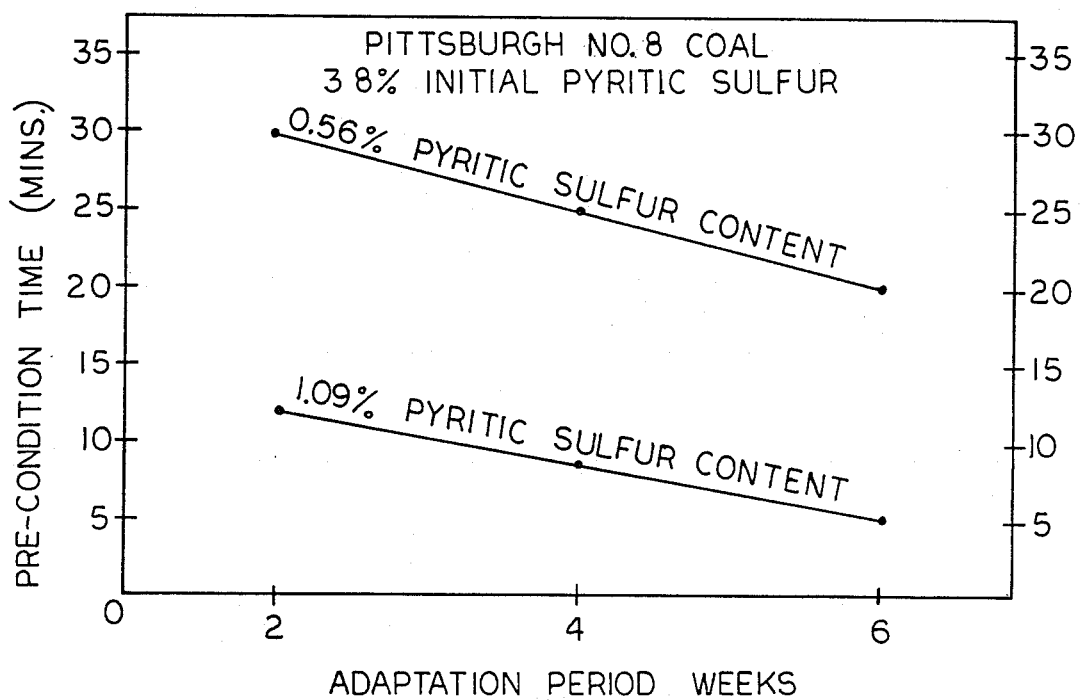
FIG. 7 EFFECT OF ADAPTATION PERIOD ON THE BACTERIAL PRE CONDITIONING TIME IN THE FLOTATION OF PITTSBURGH NO 8 COAL

COAL DESULFURIZATION USING BACTERIA ADAPTATION AND BACTERIAL MODIFICATION OF PYRITE SURFACES

FIELD OF THE INVENTION

The invention relates to coal desulfurization and more specifically to the use of bacteria for modifying the surface of pyrite particles so as to facilitate their separationn from coal via processes based on relative hydrophobicity.

BACKGROUND OF THE INVENTION

The need for environmentally acceptable energy resources remains a primary concern to industry and government, and methods for desulfurizing high sulfur coal have been one primary area of interest in this regard. While coal resources are plentiful, the quality thereof with regard to nonpolluting combustability varies from region to region. Coal quality, from the standpoint of air quality standards, is predicted principally upon the sulfur and nitrogen content thereof. There are generally three forms of sulfur in coal: (a) organic sulfur including organic sulfates, (b) pyritic sulfur, $FeS_2$, and (c) sulfate. The majority of the sulfur in most coal is in the form of iron pyrite.

The impetus for coal desulfurization can be traced to the acid rain issue and The Clean Air Act of 1970. Coal combustion plays a part in the deliberations concerning both issues. Many experts believe acidic precipitation is due to coal combustion, and much of the coal in the United States will stay in the ground until acid rain is better defined or until an efficient method for desulfurizing high sulfur coal is developed.

Most of the research into coal desulfurization has focused on pyritic sulfur, since this generally represents at least half of the sulfur in coal.

Numerous methods for desulfurizing coal have been attempted. These methods include physical separation techniques, chemical processes, and bacterial oxidation. Physical separation processes have not generally been successful, due to the smallness of particle size necessary for pyrite liberation. Chemical processes using a variety of solvents including quinoline, toluene, petroleum ether, and household bleach, have met with success in the laboratory, but these methods have not proved to be economically and technically acceptable on an industrial scale.

Thiophilic bacteria, such as *thiobacillus ferrooxidans* and *sulfolobus acidocaldarius,* have been a major area of interest due to their ability to dissolve the pyrite from the coal by oxidizing pyritic sulfur to soluble sulfates, which may then be separated from the coal. This method consists of the total oxidation of the pyrite which may take from three to fifteen days, and has not yet proved to be economically and technically acceptable on a commercial scale.

Physical-chemical separation techniques such as oil agglomeration and froth flotation have been attempted, the latter being used commercially. These techniques for purifying coal are based generally on the relative hydrophobicity of the coal as compared to the impurities to be separated. Unfortunately, the surface chemical behavior of coal and pyrite are quite similar and therefor their relative hydrophobicity is not sufficiently different, especially under commercial separation process conditions, to provide commercially acceptable separation of pyrite from high sulfur coal. For example, in the past others have treated coal slurry with *T. ferrooxidans* bacteria for fifteen to sixty minutes and then attempted to remove the pyrite from the coal slurry by an oil agglomeration technique. The results of this technique have generally been inadequate because relatively large quantities of oil must be used in the process thus making the process unacceptably expensive. In addition, the mixing of the bacteria with oil during the agglomeration process contaminated the bacterial solution and therefor limited the number of times the bacterial solution could be reused. In addition, relatively long treatment times were required which resulted only in the removal of relatively smaller percentages of pyrite.

Froth flotation is a conventional process which has been successfully used in a variety of mineral separation processes and depends upon the difference in the surface properties of the particles which constitute the slurry. In the froth flotation process, the material is ground to liberate particles of the materials to be separated. Flotation reagents such as a collector and a frother are mixed with the slurry and the slurry is then simultaneously aerated and stirred. Collector reagent is adsorbed selectively on the surfaces of the hydrophobic minerals and the hydrophobic minerals then become attached to the ascending air bubbles where they are collected on the slurry's surface in the form of froth. The hydrophillic mineral is depressed and sinks to the bottom of the flotation cell which results in the physical separation of the minerals.

Although this froth floatation process has been widely used for coal desulfurization, results have not been satisfactory because of the incomplete separation of pyrite from coal. The separation has been incomplete in part because the surface properties of both coal and pyrite particles have relatively similar hydrophobicity and thus both tend to float readily on the aerated slurry resulting in incomplete and inadequate separation.

SUMMARY OF THE INVENTION

The invention is an improvement in methods for separating pyrite from coal and is a method of the type in which the coal is ground into particles to liberate the pyrite and the particles are thereafter separated on the basis of their differing hydrophobicity, such as for example, by froth flotation. The invention comprises adapting active thiophilic bacteria to coal pyrite by exposing the bacteria to such pyrite under conditions which are favorable for bacterial activity and growth for a period of time which is sufficient to substantially enhance the ability of the bacteria to decrease the relative hydrophobicity of pyrite particles. A culture of the adapted bacteria is then used to precondition ground coal particles which have been ground prior to separation. The ground coal particles are preconditioned by subjecting the surfaces of the pyrite particles to the adapted thiophilic bacteria under conditions which are favorable for bacterial activity and growth for a period of time to permit the bacteria to act upon at least a substantial portion of the surface area of the pyrite. The bacterial action is selective towards pyrite while the coal remains unaffected. This substantially reduces the hydrophobicity of the pyrite particles making them more hydrophillic so that an increased proportion can be separated. The ground coal after being preconditioned in this manner is then subjected to a conventional separation treatment such as froth flotation.

By adapting the bacteria in this manner for a time period on the order of weeks, the preconditioning time of the commercial processing can be reduced from the three to fifteen days required for present day techniques to minutes on the order of five to fifteen minutes thus greatly increasing the through put rate of the commercial process while substantially enhancing the efficiency of separation of the sulfur bearing pyrite from the coal. Following preconditioning, the bacteria and the water may be removed from the coal being processed and reused many times without the necessity of further adaptation. They may be reused because they are not contaminated by any constituent material used in the process.

Furthermore the method of the present invention does not require care of the bacteria, the introduction of additional nutrients, reinoculation, purification or the use of substantial heat energy to maintain the bacteria at a temperature at which they operate efficiently.

Thus it is a principal object of the present invention to increase the level of pyrite rejection in the separation process while decreasing the processing time and cost so that it becomes commercially feasible.

BRIEF DESCRIPTION OF THE DRAWINGS

FIG. 2-7 are graphs of experimental data as identified on the figures.

DETAILED DESCRIPTION

Figure 1:
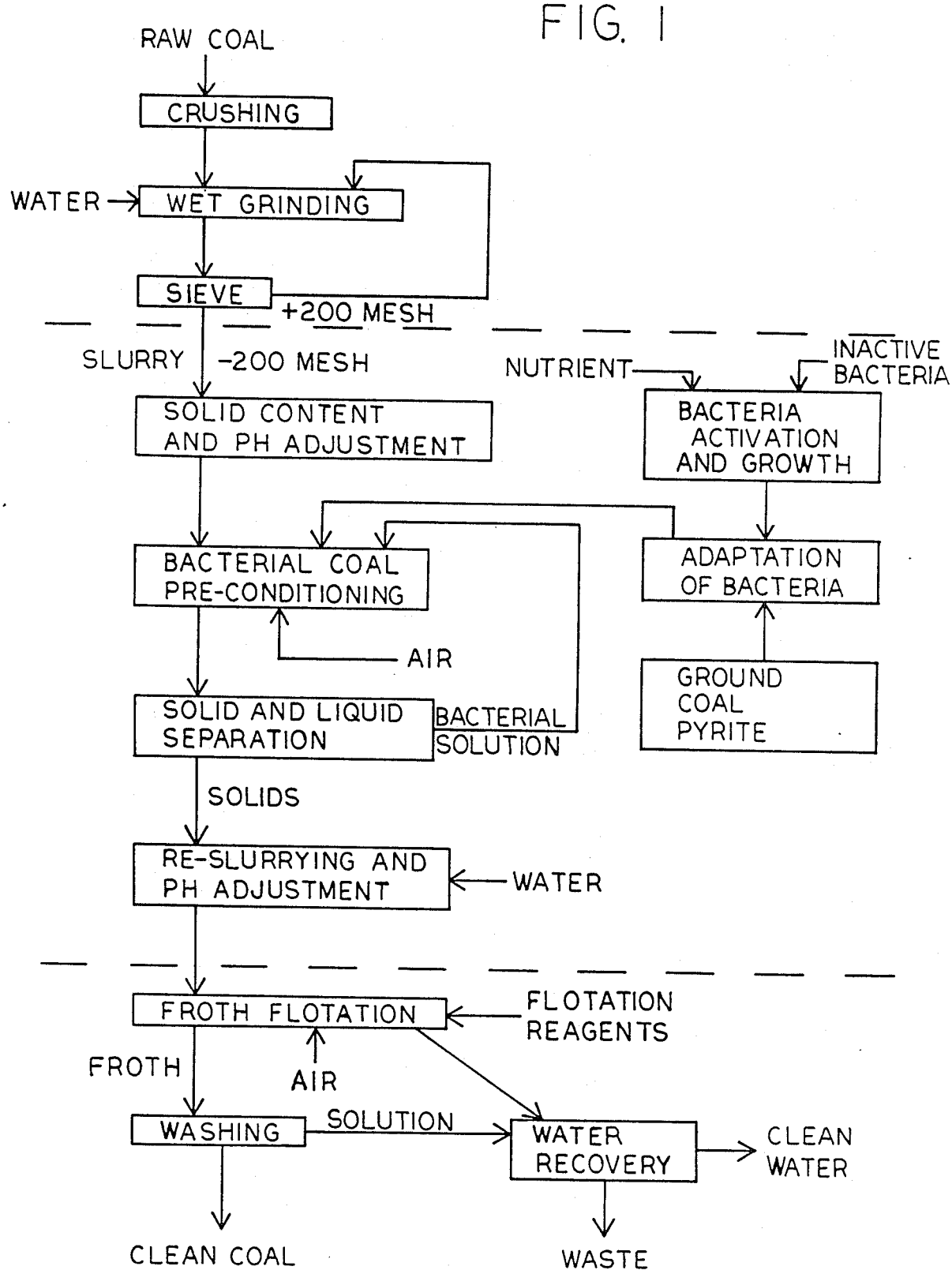
FIG. 1 is a flow chart illustrating the various steps of the method of the invention.

FIG. 1 illustrates a method embodying the present invention for separating pyrite from coal. The method of the present invention includes conventional processing steps into which the steps of the present invention are inserted. In particular, the steps of the present invention are illustrated between the horizontal dashed lines. In a conventional froth flotation process all the steps between the horizontal dashed lines are absent and instead there is a direct verticle connection to bridge the gap.

In conventional froth flotation separation as in other separation techniques, raw coal 10 is crushed at step 12 and then ground with water at step 14. Following grinding, the ground slurry is applied to a sieve 16 so that the larger particles can be returned for additional grinding while the smaller particles are passed on the next processing step. In the present invention we have used a two hundred mesh screen for separation. In conventional separation techniques the finely ground particles in the form of a slurry is passed directly to the froth flotation step 26 or other prior art process for separation.

However, in the present invention, a sample of thiophilic bacteria must first be obtained, ordinarily in an inactive state. In the present invention we have found that *Thiobacillus ferrooxidans* TFI-35 appears to give the most desirable results. However, other thiophilic bacteria such as sulfolobus acidocaldarius and thiobacillus thiooxidans should be expected to be effective. *Thiobacillus ferrooxidans* is preferred because it is effective and is very active at temperatures of substantially 30 C.

The bacteria is activated in a conventional manner such as by placing it in a flask mixed with double distilled water and a suitable nutrient medium while air is bubbled through the solution.

The *Thiobacillus ferrooxidans* strain TFI-35, which we obtained, was originally grown on a ferrous sulfate medium and was activated using 10 milliliters of stored bacteria, 20 milliliters of Tuovinen and Kelly's nutrient medium and 70 milliliters of double distilled water. This nutrient solution may be prepared by first preparing a solution A by dissolving 0.5 grams of potassium phosphate, magnesium sulfate and ammonium sulfate in a liter of 0.01 N of sulfuric acid. A solution B is prepared by dissolving 167 grams of ferrous sulfate in a liter of 1N, sulfuric acid. The nutrient solution is then prepared by mixing four parts solution A with one part of solution B. The pH of the bacterial solution was adjusted to 2.0 and maintained at a temperature of 30° C. while it was shaken and aerated with air bubbling.

After the thiophilic bacteria has been activated in this conventional manner, as illustrated at step 34, the active thiophilic bacteria is then adapted to coal pyrite at step 36. It is adapted by exposing the bacteria to coal pyrite under conditions which are favorable for bacterial activity and growth. The coal pyrite, at step 13, to which the bacteria is exposed may be, and preferably is, obtained from the commercial processing, although pure pyrite crystals from non-coal sources may be used. It is desirable that the pyrite used for adaptation has a relatively high concentration of pyrite in order that the adaptation process be efficient. While adaptation can be done with ground coal resulting from step 12, adaptation is more efficient with higher concentrations of pyrite than naturally occurs in coal. Pure pyrite could be used. We have found it most expedient to hand select pieces of pyrite in the coal mine or produced by the crushing step 12 using the Pittsburgh No. 8 coal. Such selection provides a pyrite concentration of about 60% which works well. The selected pieces of pyrite are then ground into a powder.

The bacteria is mixed with the pyrite powder (−200 mesh) and adapted for a period of time which is sufficient to substantially enhance the ability of the bacteria to decrease the relative hydrophobicity of pyrite particles.

In an adapting of the invention, the grown culture is admixed with a slurry of the pyrite powder, or of the coal pyrite powder, with the slurry mixture stirred and aerated and at an initial pH level below 4.0 and a temperature substantially in the range of 25°–35° C. More particularly, the initial pH may be in the range of 2.0 to 2.5 and the temperature is substantially 30° C.

We have found that an extended period of adaptation on the order of weeks, and preferably at least six weeks, enables the bacteria, when subsequently used in the commercial processing, to substantially reduce the hydrophobicity of, that is make more hydrophillic, the ground coal-pyrite being processed and separated.

The adapting step is carried forth for a time period of at least one week, desirably for at least two weeks, and most desirably for the at least six weeks.

By way of example we have adapted 200 milliliters of bacterial solution which was activated as described above with 50 grams of pyrite and 1000 milliliters of double distilled water. The pH was adjusted to 2.0 at the initiation of the adaptation and then permitted to vary naturally. The pH is adjusted by the appropriate addition of sulfuric acid or potassium hydroxide, for example, in the conventional manner.

We have found that the time required for the subsequent bacterial coal preconditioning step 20 is dependant upon the time of adaptation. An adaptation period of two weeks will produce an advantageous decrease in the hydrophobicity of the coal being treated in the preconditioning step 20. However, an adaptation period of at least six weeks reduces the time period during which the hydrophobicity of the pyrite may be substantially decreased to a preconditioning time period on the order of five to fifteen minutes.

No special nutrients need be added during the adaptation. Rather it is desirable to simulate the conditions of the subsequent preconditioning. During preconditioning the solution is subjected to vigorous stirring and air bubbling through the solution.

Although we do not know exactly why this adaptation period substantially enhances the speed and ability of the bacteria to reduce the hydrophobicity of the pyrite particles during bacterial coal preconditioning 20, we theorize that one or more of the following phenomena are occuring. There may be a natural selection occuring to the adaptation period causing the most effective bacteria to be selected. The bacteria may be acquiring a tolerance to metal ions and other substances in their environment. Their growth may be stimulated and metabolic products could be produced which help in modifying the surface properties of the pyrite particles when added to the coal slurry.

Although the exact mechanism by which the bacterial culture modifies the surface of the pyrite particles during the pre-conditioning step so as to render them hydrophillic is not known, some hypothetical explanations can be offered. *Thiobacillus ferrooxidans* is capable of oxidizing the pyrite and other sulfur components. Surface oxidation would change the adsorbtion and flotation behavior of the pyrite. In this case however where fuel oil is used as the flotation collector, this surface oxidation is not likely to be the only operating mechanism.

The bacterial depression effect might also be explained by the fact that *Thiobacillus ferrooxidans* are capable of producing surface active and polymeric substances, mainly polysacharides and lipids, which could adsorb onto the surfaces of sulfide mineral substrates. Since the pyrite is a substrate, it should be possible to modify its surfaces to be more wettable or hydrophillic by microbial growth. Such growth is likely to cover the pyrite surface with the bacterial cells or with the cell excreted compounds. The net effect of this bioadsorbtion will be the depression of pyrite flotation. This bioadsorbtion process is believed to be rapid enough to be done in a matter of a few minutes.

After the bacteria has been adapted for a suitable period, they are then ready for use in the commercial processing of the coal. In the commercial separation of coal in accordance with the present invention, the solid content of the slurry which passes through the sieve 16 is then adjusted by the addition or removal of water. Additionally its pH is adjusted by the addition of an acid or base such as described above. Above a pH level of 4.0 the bacteria become relatively inactive. Furthermore, they also become inactive or die at temperatures far removed from 30° C. as is well known in the art. A pH of 1.5 to 2.5 is optimum but the process still works well with a pH between 0.6 and 3.5. Similarly a temperature of 25° C. to 35° C. is optimum but the process is effective between 20° C. and 40° C.

Preferably the slurry is at or brought to a temperature of approximately 30° C. Since this a normal human environment temperature, little or no energy is required especially since the bacterial activity is exothermic. The slurry is inoculated with the previously adapted bacteria at the ratio of 20% by volume of the slurry so that the surfaces of the ground pyrite particles are subjected to the adapted thiophilic bacteria under conditions which are favorable for bacterial activity and growth. During the preconditioning step 20, the slurry mixture is preferably stirred vigorously and aerated by bubbling. No further pH adjustment is then made after initiation of the preconditioning period.

Preconditioning under these conditions continues for a period of time to permit the bacteria to act upon a substantial portion of the surface area of the pyrite particles. In commercial processing, it is desirable that this period be as brief as possible. One of the major problems with other biological coal separation techniques is that several days are required for processing. Typically, three to fifteen days is not unusual. A principal advantage of the present invention is that it reduces the bacterial processing time to minutes and typically to a time between five and thirty minutes.

Following preconditioning, the solid and liquid materials are separated. Initially the bubbling and stirring is halted and the solid particles are permitted to settle. The bacterial water solution is then removed, for example by filtering and/or centrifuging.

Because no contaminating material such as oil or flotation reagents are introduced into the processing, the bacterial solution may be recirculated, recycled and reused in the bacterial coal preconditioning step 20, after the initial bacterial activation and growth step 34 and adaptation period 36. We are currently unaware of a limitation on the number of reuses. Of course the activation and growth step 34 and the adaptation step 36 may be continuously performed to provide adapted bacteria to supplement the recycled bacterial solution.

The solid particles, which are separated from the bacterial solution at step 22, are then reslurried by the addition of clean water and the pH is adjusted in accordance with conventional principles of froth flotation. Thereafter the coal particles are separated from the pyrite particles by conventional froth flotation in the conventional manner.

In the conventional froth flotation, flotation reagents are mixed with the slurry prior to separation. The flotation reagents include a frother such as an alcohol, for example MIBC, which prevents coalescence of the air bubbles by providing a strengthened film and a collector such as oil. The oil, such as fuel oil, is added at a rate of approximately one to fifteen pounds per ton of solids and preferably one to two pounds per ton for some coal. The oil is adsorbed on any oxidized surfaces of the coal to increase the hydrophobicity of the coal in accordance with known principles. The preferred mixture of flotation reagents is MIBC and fuel oil in a 1:2 ratio.

Thereafter the slurry mixed with the flotation reagents is stirred and air is bubbled through the mixture so that the hydrophobic coal adheres to the ascending air bubbles and is collected at the upper surface of the slurry as a froth while the relatively hydrophillic pyrite particles, having been made considerably more hydrophillic by the bacterial preconditioning, settle to the bottom of the slurry. These are then separated by conventional froth flotational principles as illustrated in FIG. 1.

The bacteria can be reused for an unlimited time without any need for nutrients, reinoculation or purification because there is no contamination from the froth flotation. In addition, the froth flotation process itself is well known and accepted in the industry and is recognized as being relatively economical. Froth flotation equipment currently exists and is being utilized and therefore the present invention is easily integrated into existing commercial practice.

EXPERIMENTAL RESULTS

Before carrying out the following experiments, two samples of high sulfur coal were wet ground to −200 mesh using a stainless steel ball mill for use in the experiments. Upper Freeport coal from Armstrong County Pennsylvania had a total sulfur content of 2.10%, pyritic sulfur of 1.59% and 18.86% ash. Pittsburgh number 8 coal had a total sulfur content of 4.42%, pyritic sulfur of 3.80% and 33.89% ash.

*Thiobacillus ferrooxidans*, strain TFI-35, originally grown on ferrous sulfate medium and obtained from microbiological science department of the Ohio State University, was used to prepare activated culture samples. Bacteria, Tuovinen and Kelly's nutrient medium, and double distilled water were mixed in a 1:2:7 ratio. The pH of the solution was adjusted to 2.0 using KOH and $H_2SO_4$. The bacteria were left to activate and grow at 30° C. on a shaking water bath of 100 strokes per minute and aerated with air bubbling.

Culture samples activated in that manner were adapted to pyrite as a nutrient source and to coal pyrite modification conditions. For adaptation, the cultures were grown on ground coal pyrite originally sorted from crushed high sulfur coal of Pittsburgh number 8. This sample had a 60% pyrite content. Water, bacteria and pyrite were mixed in a 20:5:1 ratio. The pH was adjusted to 2.0 with KOH and $H_2SO_4$ and the bacteria were left to adapt and grow at 30° C. with aeration and vigorous stirring with air bubbling. One group of culture samples were adapted under these conditions for two weeks, another group for four weeks and a third group for six weeks under these conditions. The bacterial solution was then filtered on a Buckner funnel and the clean bacterial filtrate was ready for use on the coal slurry.

Ground coal was slurried with water and the pH adjusted to 2.0 with $H_2SO_4$ and KOH. Bacterial preconditioning of the coal slurry was carried out, by admixing the slurried pyrite-containing coal with the bacterial culture. Water was added and the pH was again adjusted to 2.0 with $H_2SO_4$ and KOH. For example, about 75 grams of ground coal sample was mixed with 300 ml of adapted bacteria filtrate to make 1.5 liters of slurry with about 5% solids. The temperature was maintained at 30° C. while the slurry was aerated by air bubbling and simultaneously stirred vigorously by a mechanical mixer. The mixing continued, and the resultant composition remained in admixture during the preconditioning period. Coal slurry samples were preconditioned in this manner for different preconditioning periods varying between 5 and 30 minutes. This was done to both the Upper Freeport and the Pittsburgh No. 8 coals.

Mixing then ceased, and the slurry was allowed to settle into a solid portion of the composition. The remaining liquid portion or solution was siphoned off and filtered to collect any remaining solid portion. The liquid portion contained the bacteria, and was recycled for more preconditioning after adding 50 ml of original adapted bacterial solution.

The solid portion of the composition, or thick preconditioned coal slurry, was then reslurried with water to make 1.5 liters, and the pH adjusted to the coal natural value. This pH is 8.0 for Pittsburgh number 8 coal and 8.5 for Upper Freeport coal roughly. The resultant coal slurry contained about 5% solids.

The preconditioned, pyrite-containing coal slurry was now ready to be subjected to the froth flotation process. The slurry was mixed with the froth flotation reagents, methylisobutylcarbinol or MIBC and fuel oil in a 1:2 ratio. The MIBC is the frother and fuel oil is the collector. The amount of flotation reagents added depends on the type of coal being floated, and on the flotability of that coal. Coal recovery increases with increased amounts of flotation reagent dosage, and an optimum economic amount should be determined for each coal. This was done and is discussed in connection with the experimental data. For Upper Freeport coal, the amount of flotation reagent is preferably about 1.75 lbs per ton. The amount of flotatiion reagents used for Pittsburgh number 8 coal is preferably 3 lbs per ton. In general terms, Upper Freeport coal is an easy to float coal requiring less flotation reagent dosage whereas Pittsburgh number 8 coal is a hard to float coal requiring more flotation reagent.

The slurry was allowed to condition with flotation reagents for one minute in the flotation cell, and then the froth flotation process was carried out for three minutes. Air was bubbled through the froth flotation mixture from the bottom during the process at the flow rate of 5 liters per minute, and the resultant surface phase or froth, containing the hydrophobic coal, was separated from the subsurface phase containing the hydrophillic impurities including the modified pyrite particles. Conventional froth flotation is described in a book entitled *Flotation* edited by M. C. Fuerstenau, published in 1976 by the Society of Mining Engineers.

In addition to the above experiments in which the two coal samples were subjected to a variety of preconditioning times by bacteria which had been adapted for a variety of adaptation periods, the ground coal samples prepared as described above were also subjected to froth flotation without any bacterial preconditioning. This was done not only to enable a comparison to be made between embodiments of the invention and conventional froth flotation, but also to study the flotation characteristics of the coal samples before the bacterial preconditioning. In particular it was desired to find the most efficient and economical proportion of flotation reagents which should be used.

Samples of the Upper Freeport coal and samples of the Pittsburgh No. 8 coal were subjected to conventional froth flotation in the manner described above using a variety of different proportions of the froth flotation reagent. Table 1 provides the resulting data for the Upper Freeport coal and Table 2 is the resulting data for the Pittsburgh No. 8 coal. The coal recovery percentage and pyritic sulfur rejection percentage data from Tables 1 and 2 are plotted in FIG. 2. The dosage of flotation reagent is shown in the first column of the tables. The other columns disclose the measured analysis of the ground coal samples following separation by froth flotation and the distribution of this analysis in percentage. These are plotted in FIG. 2.

Figure 2:
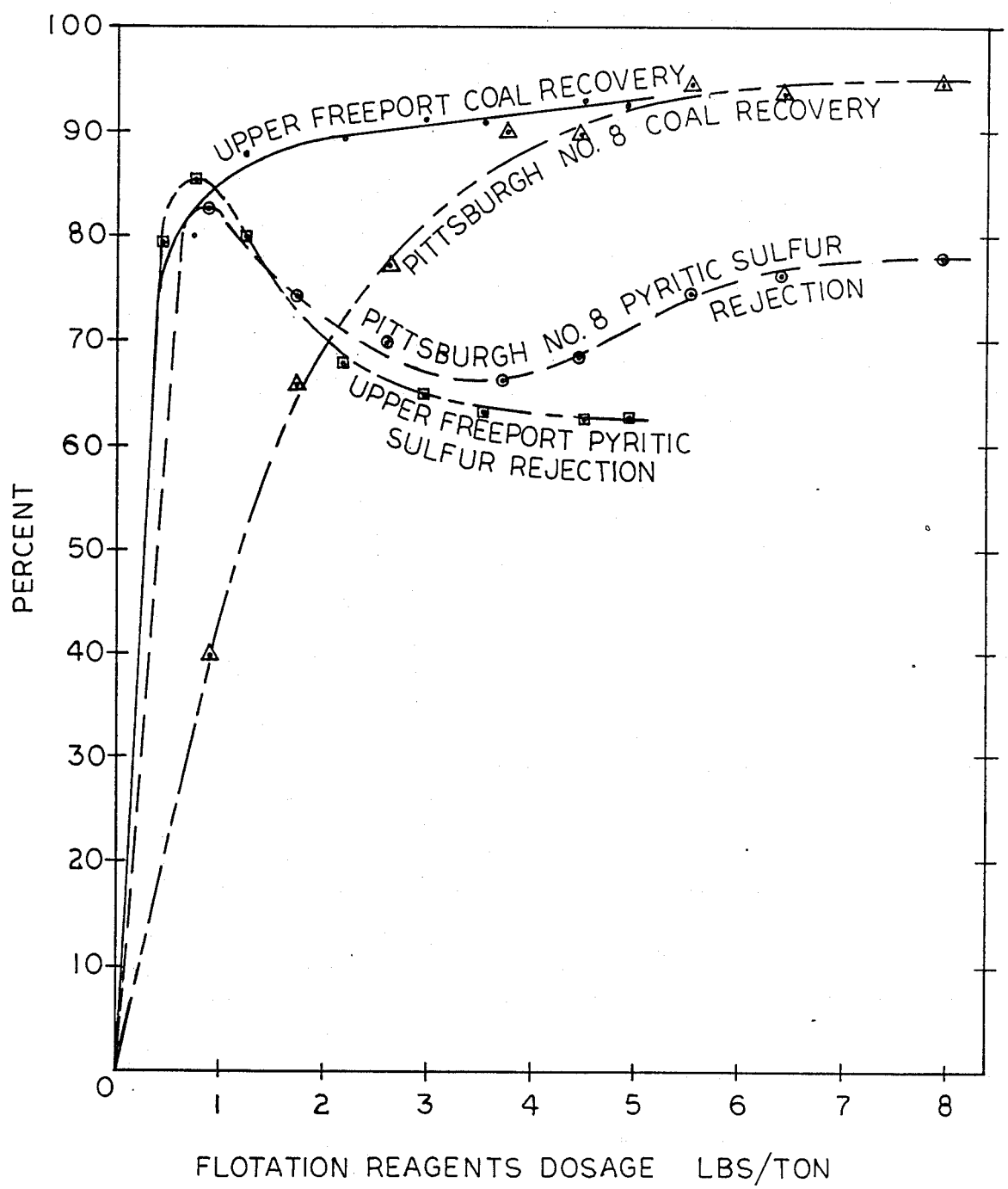

FIG. 2 shows that for Upper Freeport coal, the coal recovery improves as the proportional flotation reagent is increased. However, it also shows that above 1 lb. per ton of flotation reagent the pyritic sulfur rejection or separation is reduced. At approximately 1.75 lbs. of flotation reagent per ton of coal a reasonable compromise or engineering trade off can be made obtaining a reasonably high coal recovery and a reasonably high sulfur rejection.

the amount of 1.76 lbs. per ton and in the amount of 3 lbs. per ton for the Pittsburgh No. 8 coal.

TABLE 1
(SEE FIG. 2)
EFFECT OF FLOTATION REAGENT ON SEPARATION OF UPPER FREEPORT COAL

| FLOTATION REAGENT (LB/TON) | PRODUCT | WT % | ANALYSIS % | | | DISTRIBUTION % | | | |
|---|---|---|---|---|---|---|---|---|---|
| | | | ASH | TOTAL SULFUR | PYRITIC SULFUR | ASH | TOTAL SULFUR | PYRITIC SULFUR | COAL |
| 0.375 | FROTH | 65.93 | 11.22 | 0.91 | 0.50 | 39.2 | 28.6 | 20.7 | 72.1 |
| | TAILING | 34.07 | 33.64 | 4.40 | 3.70 | 60.8 | 71.4 | 79.3 | 27.9 |
| | FEED | 100 | 18.86 | 2.10 | 1.59 | 100 | 100 | 100 | 100 |
| 0.737 | FROTH | 71.76 | 9.41 | 0.72 | 0.32 | 35.8 | 24.6 | 14.4 | 80.1 |
| | TAILING | 28.24 | 42.87 | 5.61 | 4.82 | 64.2 | 75.4 | 85.6 | 19.9 |
| | FEED | 100 | 18.86 | 2.10 | 1.59 | 100 | 100 | 100 | 100 |
| 1.194 | FROTH | 77.50 | 8.03 | 0.85 | 0.41 | 33.0 | 31.4 | 20.0 | 87.9 |
| | TAILING | 22.50 | 56.16 | 6.41 | 5.65 | 67.0 | 68.6 | 80.0 | 12.1 |
| | FEED | 100 | 18.86 | 2.10 | 1.59 | 100 | 100 | 100 | 100 |
| 2.175 | FROTH | 80.49 | 9.86 | 1.0 | 0.63 | 42.1 | 40.7 | 31.9 | 89.4 |
| | TAILING | 19.51 | 55.97 | 6.39 | 5.55 | 57.9 | 59.3 | 68.1 | 10.6 |
| | FEED | 100 | 18.86 | 2.10 | 1.59 | 100 | 100 | 100 | 100 |
| 2.975 | FROTH | 82.73 | 10.19 | 1.11 | 0.69 | 44.7 | 42.9 | 34.9 | 91.6 |
| | TAILING | 17.27 | 60.39 | 6.84 | 5.90 | 55.3 | 57.1 | 65.1 | 8.4 |
| | FEED | 100 | 18.86 | 2.10 | 1.59 | 100 | 100 | 100 | 100 |
| 3.543 | FROTH | 82.80 | 10.81 | 1.12 | 0.70 | 47.5 | 44.2 | 36.5 | 91.0 |
| | TAILING | 17.20 | 57.57 | 6.82 | 5.87 | 55.5 | 55.8 | 63.5 | 9.0 |
| | FEED | 100 | 18.86 | 2.10 | 1.59 | 100 | 100 | 100 | 100 |
| 1.540 | FROTH | 84.82 | 10.93 | 1.16 | 0.70 | 49.2 | 46.9 | 37.3 | 93.1 |
| | TAILING | 15.18 | 63.17 | 7.35 | 6.56 | 50.8 | 53.1 | 62.7 | 6.9 |
| | FEED | 100 | 18.86 | 2.10 | 1.59 | 100 | 100 | 100 | 100 |
| 1.817 | FROTH | 84.60 | 11.08 | 1.15 | 0.69 | 49.7 | 46.3 | 37.1 | 92.7 |
| | TAILING | 15.40 | 61.60 | 7.32 | 6.49 | 50.3 | 53.7 | 62.9 | 7.3 |
| | FEED | 100 | 18.86 | 2.10 | 1.59 | 100 | 100 | 100 | 100 |

TABLE 2
(SEE FIG. 2)
EFFECT OF FLOTATION REAGENT ON SEPARATION OF PITTSBURGH NO. 8 COAL

| FLOTATION REAGENT (LB/TON) | PRODUCT | WT % | ANALYSIS % | | | DISTRIBUTION % | | | |
|---|---|---|---|---|---|---|---|---|---|
| | | | ASH | TOTAL SULFUR | PYRITIC SULFUR | ASH | TOTAL SULFUR | PYRITIC SULFUR | COAL |
| 0.835 | FROTH | 32.35 | 19.22 | 2.63 | 2.02 | 18.3 | 19.2 | 17.2 | 39.5 |
| 0.835 | TAILING | 67.63 | 40.92 | 5.28 | 4.65 | 81.7 | 80.8 | 82.8 | 60.5 |
| 0.835 | FEED | 100 | 33.89 | 4.42 | 3.80 | 100 | 100 | 100 | 100 |
| 1.714 | FROTH | 53.37 | 18.42 | 2.45 | 1.84 | 29.0 | 29.6 | 25.8 | 65.9 |
| 1.714 | TAILING | 46.63 | 51.60 | 6.67 | 6.04 | 71.0 | 70.4 | 74.2 | 34.1 |
| 1.714 | FEED | 100 | 33.89 | 4.42 | 3.80 | 100 | 100 | 100 | 100 |
| 2.612 | FROTH | 64.08 | 19.83 | 2.43 | 1.79 | 37.5 | 35.2 | 30.3 | 77.7 |
| 2.612 | TAILING | 35.92 | 58.96 | 7.97 | 7.37 | 62.5 | 64.8 | 69.7 | 22.3 |
| 2.612 | FEED | 100 | 33.89 | 4.42 | 3.80 | 100 | 100 | 100 | 100 |
| 3.666 | FROTH | 71.71 | 16.96 | 2.37 | 1.80 | 35.9 | 38.5 | 33.0 | 90.0 |
| 3.666 | TAILING | 28.29 | 76.79 | 9.52 | 8.76 | 64.1 | 61.5 | 66.0 | 10.0 |
| 3.666 | FEED | 100 | 33.89 | 4.42 | 3.80 | 100 | 100 | 100 | 100 |
| 4.475 | FROTH | 70.15 | 15.65 | 2.31 | 1.72 | 32.4 | 36.7 | 31.7 | 89.5 |
| 4.475 | TAILING | 29.85 | 76.75 | 9.38 | 8.69 | 67.6 | 63.3 | 68.3 | 10.5 |
| 4.475 | FEED | 100 | 33.89 | 4.42 | 3.80 | 100 | 100 | 100 | 100 |
| 5.546 | FROTH | 73.38 | 14.55 | 1.96 | 1.33 | 31.5 | 32.5 | 25.7 | 94.8 |
| 5.546 | TAILING | 26.62 | 87.20 | 11.20 | 10.61 | 68.5 | 67.5 | 74.3 | 5.2 |
| 5.546 | FEED | 100 | 33.89 | 4.42 | 3.80 | 100 | 100 | 100 | 100 |
| 6.369 | FROTH | 73.75 | 15.95 | 1.83 | 1.22 | 34.7 | 30.5 | 23.7 | 93.8 |
| 6.369 | TAILING | 26.25 | 84.29 | 11.70 | 11.05 | 65.3 | 69.5 | 76.3 | 6.2 |
| 6.639 | FEED | 100 | 33.89 | 4.42 | 3.80 | 100 | 100 | 100 | 100 |
| 7.928 | FROTH | 76.28 | 17.68 | 1.72 | 1.10 | 39.8 | 29.7 | 22.1 | 94.9 |
| 7.928 | TAILING | 23.72 | 86.02 | 13.10 | 12.48 | 60.2 | 70.3 | 77.9 | 5.1 |
| 7.928 | FEED | 100 | 33.89 | 4.42 | 3.80 | 100 | 100 | 100 | 100 |

For Pittsburgh No. 8 coal, the reasonable trade off is about 3 lbs. of flotation reagent per ton of coal. Above these quantities of flotation reagents relatively small gains are made in separation at the expense of the consumption of additional flotation reagents. Therefore, in the remaining data for all froth flotation processes which followed bacterial adaptation and coal preconditioning in accordance with the present invention, the flotation reagent was used with Upper Freeport coal in The effect of the bacterial preconditioning period and the adaptation period on the effectiveness of the separation process were studied. In order to determine the most effective bacterial preconditioning period and adaptation period the three bacterial samples, which were adapted for two, four and six weeks respectively on the coal pyrite, were used. Tables 3 and 4 illustrate the results adapted for two weeks, Tables 5 and 6 illustrate the results for bacteria adapted for four weeks and Tables 7 and 8 illustrate the results for bacteria adapted for six weeks.

Tables 3 and 4 illustrate the data showing the analysis of coal samples after being subjected to preconditioning for the times stated in the first column of those tables and using bacteria which had been adapted for two weeks. Preconditioning times of five, ten, fifteen, twenty, twenty five, and thirty minutes were used. These are shown in the first column of Tables 3–8.

FIG. 3 is a graph of the coal recovery and pyritic sulfur rejection for both types of coal using two week adapted bacteria and the data from Tables 3 and 4.

Similarly, FIG. 4 illustrates the coal recovery and pyritic sulfur rejection for both types of coal using bacteria adapted for a period of four weeks and plotted from the data of Tables 5 and 6. Similarly, FIG. 5 is a graph of the coal recovery and pyritic sulfur rejection for both types of coal using bacteria adapted for six weeks and plotted from the data of Tables 7 and 8.

TABLE 3

(SEE FIG. 3)
EFFECT OF PRECONDITIONING TIME ON SEPARATION OF
UPPER FREEPORT COAL WITH BACTERIA
ADAPTED FOR 2 WEEKS

| PRECONDITION TIME (MINUTES) | PRODUCT | WT % | ANALYSIS % | | | DISTRIBUTION % | | | |
|---|---|---|---|---|---|---|---|---|---|
| | | | ASH | TOTAL SULFUR | PYRITIC SULFUR | ASH | TOTAL SULFUR | PYRITIC SULFUR | COAL |
| 0(conventional | FROTH | 79.55 | 8.75 | 1.12 | 0.57 | 36.9 | 42.4 | 28.5 | 89.5 |
| 0 froth flot. | TAILING | 20.45 | 58.18 | 5.91 | 5.55 | 63.1 | 57.6 | 71.5 | 10.5 |
| 0 only) | FEED | 100 | 18.86 | 2.10 | 1.59 | 100 | 100 | 100 | 100 |
| 5 | FROTH | 78.19 | 7.98 | 0.95 | 0.40 | 33.1 | 35.4 | 19.7 | 88.6 |
| 5 | TAILING | 21.81 | 57.86 | 6.22 | 5.85 | 66.9 | 64.6 | 80.3 | 11.4 |
| 5 | FEED | 100 | 18.86 | 2.10 | 1.59 | 100 | 100 | 100 | 100 |
| 10 | FROTH | 77.39 | 7.76 | 0.90 | 0.36 | 31.8 | 33.2 | 17.5 | 87.9 |
| 10 | TAILING | 22.61 | 56.85 | 6.20 | 5.80 | 68.2 | 66.8 | 82.5 | 12.1 |
| 10 | FEED | 100 | 18.86 | 2.10 | 1.59 | 100 | 100 | 100 | 100 |
| 15 | FROTH | 76.25 | 7.52 | 0.83 | 0.30 | 30.0 | 30.1 | 14.4 | 86.9 |
| 15 | TAILING | 23.75 | 55.26 | 6.17 | 5.73 | 70.0 | 69.9 | 85.6 | 13.1 |
| 15 | FEED | 100 | 18.86 | 2.10 | 1.59 | 100 | 100 | 100 | 100 |
| 20 | FROTH | 75.98 | 7.23 | 0.80 | 0.28 | 29.1 | 28.9 | 13.4 | 86.8 |
| 20 | TAILING | 24.75 | 54.00 | 6.02 | 5.56 | 70.9 | 71.1 | 86.6 | 13.2 |
| 20 | FEED | 100 | 18.86 | 2.10 | 1.59 | 100 | 100 | 100 | 100 |
| 25 | FROTH | 75.48 | 6.91 | 0.75 | 0.22 | 27.6 | 26.9 | 10.4 | 86.6 |
| 25 | TAILING | 24.52 | 55.64 | 6.25 | 5.80 | 72.4 | 73.1 | 89.6 | 13.4 |
| 25 | FEED | 100 | 18.86 | 2.10 | 1.59 | 100 | 100 | 100 | 100 |
| 30 | FROTH | 75.45 | 6.62 | 0.72 | 0.20 | 26.5 | 25.8 | 9.4 | 86.8 |
| 30 | TAILING | 24.55 | 56.47 | 6.34 | 5.86 | 73.5 | 74.2 | 90.6 | 13.2 |
| 30 | FEED | 100 | 18.86 | 2.10 | 1.59 | 100 | 100 | 100 | 100 |

TABLE 4

(SEE FIG. 3)
EFFECT OF PRECONDITIONING TIME ON SEPARATION
OF PITTSBURGH NO. 8 COAL

| PRECONDITION TIME (MINUTES) | PRODUCT | WT % | ANALYSIS % | | | DISTRIBUION % | | | |
|---|---|---|---|---|---|---|---|---|---|
| | | | ASH | TOTAL SULFUR | PYRITIC SULFUR | ASH | TOTAL SULFUR | PYRITIC SULFUR | COAL |
| 0 (conventional | FROTH | 66.92 | 19.78 | 2.59 | 1.86 | 39.0 | 39.2 | 32.7 | 81.2 |
| 0 froth flot. | TAILING | 33.08 | 62.43 | 8.12 | 7.72 | 61.0 | 60.8 | 67.3 | 18.8 |
| 0 only) | FEED | 100 | 33.89 | 4.42 | 3.80 | 100 | 100 | 100 | 100 |
| 5 | FROTH | 64.77 | 18.32 | 2.05 | 1.39 | 35.00 | 30.0 | 23.7 | 80.0 |
| 5 | TAILING | 35.23 | 62.51 | 8.77 | 8.23 | 65.0 | 70.0 | 76.3 | 20.0 |
| 5 | FEED | 100 | 33.89 | 4.42 | 3.80 | 100 | 100 | 100 | 100 |
| 10 | FROTH | 63.96 | 18.20 | 1.79 | 1.11 | 34.3 | 25.9 | 18.6 | 79.1 |
| 10 | TAILING | 36.04 | 61.73 | 9.08 | 8.57 | 65.7 | 74.1 | 81.4 | 20.9 |
| 10 | FEED | 100 | 33.89 | 4.42 | 3.80 | 100 | 100 | 100 | 100 |
| 15 | FROTH | 63.08 | 17.80 | 1.66 | 1.03 | 33.1 | 23.6 | 17.1 | 78.4 |
| 15 | TAILING | 36.92 | 61.38 | 9.14 | 8.53 | 66.9 | 76.4 | 82.9 | 21.6 |
| 15 | FEED | 100 | 33.89 | 4.42 | 3.80 | 100 | 100 | 100 | 100 |
| 20 | FROTH | 62.57 | 17.00 | 1.53 | 0.86 | 31.3 | 21.6 | 14.1 | 78.6 |
| 20 | TAILING | 37.43 | 62.12 | 9.25 | 8.71 | 68.7 | 78.4 | 85.9 | 21.4 |
| 20 | FEED | 100 | 33.89 | 4.42 | 3.80 | 100 | 100 | 100 | 100 |
| 25 | FROTH | 62.12 | 16.70 | 1.36 | 0.68 | 30.6 | 19.1 | 11.1 | 78.2 |
| 25 | TAILING | 37.88 | 62.08 | 9.43 | 8.91 | 69.4 | 80.9 | 88.9 | 21.8 |
| 25 | FEED | 100 | 33.89 | 4.42 | 3.80 | 100 | 100 | 100 | 100 |
| 30 | FROTH | 61.40 | 16.20 | 1.22 | 0.56 | 29.3 | 16.9 | 9.0 | 77.8 |
| 30 | TAILING | 38.60 | 62.02 | 9.51 | 8.95 | 70.7 | 83.1 | 91.0 | 22.2 |
| 30 | FEED | 100 | 33.89 | 4.42 | 3.80 | 100 | 100 | 100 | 100 |

TABLE 5

(SEE FIG. 4)
EFFECT OF PRECONDITIONING TIME ON SEPARATION OF
UPPER FREEPORT COAL WITH BACTERIA
ADAPTED FOR 4 WEEKS

| PRECONDITION TIME (MINUTES) | PRODUCT | WT % | ANALYSIS % | | | DISTRIBUTION % | | | COAL |
|---|---|---|---|---|---|---|---|---|---|
| | | | ASH | TOTAL SULFUR | PYRITIC SULFUR | ASH | TOTAL SULFUR | PYRITIC SULFUR | |
| 0 (conventional | FROTH | 81.32 | 9.15 | 1.15 | 0.58 | 39.5 | 44.5 | 29.7 | 91.0 |
| 0 froth flot. | TAILING | 18.68 | 61.13 | 6.23 | 5.98 | 60.5 | 55.5 | 70.3 | 9.0 |
| 0 only) | FEED | 100 | 18.86 | 2.10 | 1.59 | 100 | 100 | 100 | 100 |
| 5 | FROTH | 79.2 | 8.40 | 0.85 | 0.31 | 35.3 | 32.0 | 15.4 | 89.4 |
| 5 | TAILING | 20.80 | 58.68 | 6.86 | 6.46 | 64.7 | 68.0 | 84.6 | 10.6 |
| 5 | FEED | 100 | 18.86 | 2.10 | 1.59 | 100 | 100 | 100 | 100 |
| 10 | FROTH | 78.18 | 8.02 | 0.80 | 0.27 | 33.2 | 29.8 | 13.3 | 88.6 |
| 10 | TAILING | 21.82 | 57.72 | 6.75 | 6.32 | 66.8 | 70.2 | 86.7 | 11.4 |
| 10 | FEED | 100 | 18.86 | 2.10 | 1.59 | 100 | 100 | 100 | 100 |
| 15 | FROTH | 77.46 | 7.70 | 0.75 | 0.23 | 31.6 | 27.7 | 11.2 | 88.1 |
| 15 | TAILING | 22.54 | 57.21 | 6.74 | 6.26 | 68.4 | 72.3 | 88.8 | 11.9 |
| 15 | FEED | 100 | 18.86 | 2.10 | 1.59 | 100 | 100 | 100 | 100 |
| 20 | FROTH | 76.86 | 7.05 | 0.71 | 0.17 | 28.7 | 26.0 | 8.2 | 88.0 |
| 20 | TAILING | 23.14 | 58.09 | 6.71 | 6.30 | 71.3 | 74.0 | 91.8 | 12.0 |
| 20 | FEED | 100 | 18.86 | 2.10 | 1.59 | 100 | 100 | 100 | 100 |
| 25 | FROTH | 75.70 | 6.52 | 0.69 | 0.16 | 26.2 | 24.9 | 7.6 | 87.2 |
| 25 | TAILING | 24.30 | 57.30 | 6.49 | 6.04 | 73.8 | 75.1 | 92.4 | 12.8 |
| 25 | FEED | 100 | 18.86 | 2.10 | 1.59 | 100 | 100 | 100 | 100 |
| 30 | FROTH | 75.00 | 6.02 | 0.66 | 0.15 | 23.9 | 23.5 | 7.0 | 86.8 |
| 30 | TAILING | 25.00 | 57.38 | 6.42 | 5.91 | 76.1 | 76.5 | 93.0 | 13.2 |
| 30 | FEED | 100 | 18.86 | 2.10 | 1.59 | 100 | 100 | 100 | 100 |

TABLE 6

(SEE FIG. 4)
EFFECT OF PRECONDITIONING TIME ON SEPARATION OF
PITTSBURGH NO. 8 COAL
ADAPTED FOR 4 WEEKS

| PRECONDITION TIME (MINUTES) | PRODUCT | WT % | ANALYSIS % | | | DISTRIBUTION % | | | COAL |
|---|---|---|---|---|---|---|---|---|---|
| | | | ASH | TOTAL SULFUR | PYRITIC SULFUR | ASH | TOTAL SULFUR | PYRITIC SULFUR | |
| 0 (conventional | FROTH | 67.58 | 20.12 | 2.63 | 1.93 | 40.1 | 40.2 | 34.3 | 81.7 |
| 0 froth flot. | TAILING | 32.42 | 62.59 | 8.15 | 7.69 | 59.9 | 59.8 | 65.7 | 18.3 |
| 0 only) | FEED | 100 | 33.89 | 4.42 | 3.80 | 100 | 100 | 100 | 100 |
| 5 | FROTH | 64.29 | 18.95 | 1.84 | 1.21 | 35.9 | 26.8 | 20.5 | 78.8 |
| 5 | TAILING | 35.29 | 61.51 | 9.17 | 8.56 | 64.1 | 73.2 | 79.5 | 21.2 |
| 5 | FEED | 100 | 33.89 | 4.42 | 3.80 | 100 | 100 | 100 | 100 |
| 10 | FROTH | 63.55 | 18.40 | 1.72 | 1.07 | 34.5 | 24.7 | 17.9 | 78.4 |
| 10 | TAILING | 36.45 | 60.90 | 9.13 | 8.56 | 65.5 | 75.3 | 82.1 | 21.6 |
| 10 | FEED | 100 | 33.89 | 4.42 | 3.80 | 100 | 100 | 100 | 100 |
| 15 | FROTH | 62.20 | 18.00 | 1.50 | 0.86 | 33.0 | 21.1 | 14.1 | 77.2 |
| 15 | TAILING | 37.80 | 60.04 | 9.22 | 8.64 | 67.0 | 78.9 | 85.9 | 22.8 |
| 15 | FEED | 100 | 33.89 | 4.42 | 3.80 | 100 | 100 | 100 | 100 |
| 20 | FROTH | 61.49 | 17.39 | 1.28 | 0.62 | 31.6 | 17.8 | 10.0 | 76.8 |
| 20 | TAILING | 38.51 | 60.24 | 9.43 | 8.88 | 68.4 | 82.2 | 90.0 | 23.2 |
| 20 | FEED | 100 | 33.89 | 4.42 | 3.80 | 100 | 100 | 100 | 100 |
| 25 | FROTH | 60.67 | 16.90 | 1.22 | 0.58 | 30.3 | 16.7 | 9.3 | 76.3 |
| 25 | TAILING | 39.33 | 60.10 | 9.36 | 8.77 | 69.7 | 83.3 | 90.7 | 23.7 |
| 25 | FEED | 100 | 33.89 | 4.42 | 3.80 | 100 | 100 | 100 | 100 |
| 30 | FROTH | 59.98 | 16.05 | 1.09 | 0.45 | 28.4 | 14.8 | 7.1 | 76.1 |
| 30 | TAILING | 40.02 | 60.62 | 9.41 | 8.82 | 71.6 | 85.2 | 92.9 | 23.9 |
| 30 | FEED | 100 | 33.89 | 4.42 | 3.80 | 100 | 100 | 100 | 100 |

TABLE 7

(SEE FIG. 5)
EFFECT OF PRECONDITIONING TIME ON SEPARATION OF
UPPER FREEPORT COAL WIIH BACTERIA
ADAPTED FOR 6 WEEKS

| PRECONDITION TIME (MINUTES) | PRODUCT | WT % | ANALYSIS % | | | DISTRIBUTION % | | | COAL |
|---|---|---|---|---|---|---|---|---|---|
| | | | ASH | TOTAL SULFUR | PYRITIC SULFUR | ASH | TOTAL SULFUR | PYRITIC SULFUR | |
| 0 (conventional | FROTH | 81.84 | 9.61 | 1.15 | 0.58 | 41.7 | 44.8 | 29.9 | 91.2 |
| 0 froth flot. | TAILING | 18.16 | 60.55 | 6.38 | 6.14 | 58.3 | 55.2 | 70.1 | 8.8 |
| 0 only) | FEED | 100 | 18.86 | 2.10 | 1.59 | 100 | 100 | 100 | 100 |
| 5 | FROTH | 78.77 | 8.79 | 0.81 | 0.27 | 36.7 | 30.4 | 13.4 | 88.5 |
| 5 | TAILING | 21.23 | 56.22 | 6.89 | 6.48 | 63.3 | 69.6 | 86.6 | 11.5 |
| 5 | FEED | 100 | 18.86 | 2.10 | 1.59 | 100 | 100 | 100 | 100 |
| 10 | FROTH | 78.12 | 7.92 | 0.75 | 0.21 | 32.8 | 27.9 | 10.3 | 88.7 |
| 10 | TAILING | 21.88 | 57.92 | 6.92 | 6.52 | 67.2 | 72.1 | 89.7 | 11.3 |

TABLE 7-continued (SEE FIG. 5)
EFFECT OF PRECONDITIONING TIME ON SEPARATION OF
UPPER FREEPORT COAL WIlH BACTERIA
ADAPTED FOR 6 WEEKS

| PRECONDITION TIME (MINUTES) | PRODUCT | WT % | ANALYSIS % | | | DISTRIBUTION % | | | |
|---|---|---|---|---|---|---|---|---|---|
| | | | ASH | TOTAL SULFUR | PYRITIC SULFUR | ASH | TOTAL SULFUR | PYRITIC SULFUR | COAL |
| 10 | FEED | 100 | 18.86 | 2.10 | 1.59 | 100 | 100 | 100 | 100 |
| 15 | FROTH | 77.54 | 7.36 | 0.73 | 0.19 | 30.2 | 26.9 | 9.3 | 88.5 |
| 15 | TAILING | 22.46 | 58.56 | 6.83 | 6.42 | 69.8 | 73.1 | 90.7 | 11.5 |
| 15 | FEED | 100 | 18.86 | 2.10 | 1.59 | 100 | 100 | 100 | 100 |
| 20 | FROTH | 76.09 | 6.90 | 0.70 | 0.16 | 27.8 | 25.4 | 7.7 | 87.3 |
| 20 | TAILING | 23.91 | 56.92 | 6.56 | 6.14 | 72.2 | 74.6 | 93.3 | 12.7 |
| 20 | FEED | 100 | 18.86 | 2.10 | 1.59 | 100 | 100 | 100 | 100 |
| 25 | FROTH | 75.20 | 6.32 | 0.68 | 0.14 | 25.2 | 24.3 | 6.6 | 86.8 |
| 25 | TAILING | 24.80 | 56.88 | 6.41 | 5.99 | 74.8 | 75.7 | 93.4 | 13.2 |
| 25 | FEED | 100 | 18.86 | 2.10 | 1.59 | 100 | 100 | 100 | 100 |
| 30 | FROTH | 75.16 | 6.00 | 0.65 | 0.13 | 23.9 | 23.3 | 6.1 | 87.1 |
| 30 | TAILING | 24.84 | 57.77 | 6.49 | 6.01 | 76.1 | 76.7 | 93.9 | 12.9 |
| 30 | FEED | 100 | 18.86 | 2.10 | 1.59 | 100 | 100 | 100 | 100 |

TABLE 8

(SEE FIG. 5)
EFFECT OF PRECONDITIONING TIME ON SEPARATION
OF PITTSBURGH NO. 8
ADAPTED FOR 6 WEEKS

| PRECONDITION TIME (MINUTES) | PRODUCT | WT % | ANALYSIS % | | | DISTRIBUTION % | | | |
|---|---|---|---|---|---|---|---|---|---|
| | | | ASH | TOTAL SULFUR | PYRITIC SULFUR | ASH | TOTAL SULFUR | PYRITIC SULFUR | COAL |
| 0 | FROTH | 67.81 | 20.61 | 2.55 | 1.90 | 41.2 | 39.1 | 33.9 | 81.4 |
| | TAILING | 32.19 | 61.87 | 8.36 | 7.80 | 58.8 | 60.9 | 66.1 | 18.6 |
| | FEED | 100 | 33.89 | 4.42 | 3.80 | 100 | 100 | 100 | 100 |
| 5 | FROTH | 64.91 | 18.86 | 1.77 | 1.09 | 36.1 | 25.9 | 18.6 | 79.7 |
| | TAILING | 35.09 | 61.69 | 9.32 | 8.81 | 63.9 | 74.1 | 81.4 | 20.3 |
| | FEED | 100 | 33.89 | 4.42 | 3.80 | 100 | 100 | 100 | 100 |
| 10 | FROTH | 63.34 | 17.55 | 1.48 | 0.85 | 32.8 | 21.2 | 14.2 | 79.0 |
| | TAILING | 36.66 | 62.12 | 9.50 | 8.90 | 67.2 | 78.8 | 85.8 | 21.0 |
| | FEED | 100 | 33.89 | 4.42 | 3.80 | 100 | 100 | 100 | 100 |
| 15 | FROTH | 62.67 | 17.02 | 1.30 | 0.63 | 31.5 | 18.4 | 10.4 | 78.7 |
| | TAILING | 37.33 | 62.21 | 9.66 | 9.12 | 68.5 | 81.6 | 89.6 | 21.3 |
| | FEED | 100 | 33.89 | 4.42 | 3.80 | 100 | 100 | 100 | 100 |
| 20 | FROTH | 61.23 | 16.53 | 1.19 | 0.55 | 29.8 | 16.5 | 8.7 | 77.3 |
| | TAILING | 38.77 | 61.31 | 9.52 | 8.93 | 70.2 | 83.5 | 91.3 | 22.7 |
| | FEED | 100 | 33.89 | 4.42 | 3.80 | 100 | 100 | 100 | 100 |
| 25 | FROTH | 59.88 | 16.04 | 1.06 | 0.42 | 28.3 | 14.3 | 6.6 | 76.0 |
| | TAILING | 40.12 | 60.53 | 9.43 | 8.84 | 71.7 | 85.7 | 93.4 | 24.0 |
| | FEED | 100 | 33.89 | 4.42 | 3.80 | 100 | 100 | 100 | 100 |
| 30 | FROTH | 58.98 | 15.92 | 0.99 | 0.36 | 27.7 | 13.2 | 5.6 | 75.0 |
| | TAILING | 41.02 | 59.72 | 9.35 | 8.74 | 72.3 | 86.8 | 94.4 | 25.0 |
| | FEED | 100 | 33.89 | 4.42 | 3.80 | 100 | 100 | 100 | 100 |

From FIG. 3 and Table 3, it is clear that the coal recovery from Upper Freeport coal with 2 week adapted bacteria is slightly effected by the bacterial pre-conditioning time; it is decreased from 89.5% at no bacterial treatment to 86.8% after 30 minutes of treatment; i.e., less than 3%. The pyritic sulfur rejection increases from 71.5% at no bacterial treatment to 90.6% after 30 minutes treatment; i.e., about 19% of pyritic sulfur was removed as a result of the bacterial treatment.

From Table 3, the total sulfur and ash rejection increased from 57.6% and 63.1% at no bacterial treatment to 74.2% and 73.5% after 30 minutes treatment respectively; i.e., the total sulfur rejection increased by 16.6% and that of ash by 10.4% due to the bacterial pre-conditioning. This is not because $T.$ $ferrooxidans$ have a direct effect on carbonaceous ash minerals or organic sulfur content, but because of its effect on the pyrite depression during the flotation test; i.e., because of the changing of ash constituents. Also, the pyritic sulfur, total sulfur and ash contents were reduced to 0.20%, 0.72%, and 6.62%, respectively.

So from the obtained results shown in Table 3, it is clear that the froth flotation with 1.75 lb/ton flotation reagents and without any bacterial treatment could decrease the pyritic sulfur content from 1.59% to 0.57% while the bacterial pre-conditioning with 2 weeks adapted bacteria could decrease pyritic sulfur content further from 0.57% to 0.20% in 30 minutes, i.e., 90.6% pyritic sulfur rejection, while the bacterial pre-conditioning could decrease the pyritic sulfur content to 0.36% in only 10 minutes; i.e., the rejection of pyritic sulfur is 82.5% after only 10 minutes pre-conditioning with 2 weeks adapted $T.$ $ferrooxidans$.

The effect of bacterial pre-conditioning time with 2 weeks adapted $T.$ $ferrooxidans$ on the coal recovery and ash, total and pyritic sulfur contents and rejections of Pittsburgh No. 8 coal slurries were studied and the results obtained are shown in FIG. 3 and Table 4. FIG. 3 shows that the coal recovery is slightly effected by bacterial preconditioning; it is decreased by about 3.4% after 30 minutes of treatment, while ash rejection increased by about 9.7% at the same pre-conditioning time. Pyritic sulfur rejection is increased by 23.7%, while pyritic sulfur content decreased from 1.86% to 0.56%; i.e., about 1.3% reduction after 30 minutes of bacterial pre-conditioning.

Table 4 shows that total sulfur rejection increased by about 22.3%, while the total sulfur content decreased from 2.59% to 1.22%; i.e., about 1.37% sulfur content reduction after 30 minutes of bacterial treatment with 2 weeks adapted *T. ferrooxidans*. From Table 4, it is clear that the froth flotation with about 3.0 lb/ton flotation reagents could decrease the pyritic sulfur content from 3.8% to 1.86%, while the bacterial pre-conditioning for 30 minutes decreases it from 1.86% to only 0.56%; i.e., about 91.0% of pyritic sulfur was removed due to the pre-conditioning with 2 weeks adapted bacteria followed by froth flotation with 3.0 lb/ton flotation reagents, while the bacterial preconditioning for only 10 minutes reduces the pyritic sulfur from 1.86% to 1.11%; i.e., about 81.4% of pyritic sulfur was removed after only 10 minutes of bacterial pre-conditioning.

For bacteria adapted for four weeks, from FIG. 4 and Table 5, it is clear that the coal recovery from Upper Freeport coal is slightly decreased as a result of bacterial pre-conditioning (about 4% after 30 minutes of pre-conditioning). Also, pyritic sulfur, total sulfur and ash rejections increase as a result of 30 min. bacterial pre-conditioning from 70.3%, 55.5%, and 60.5% to 93%, 76.5%, and 76.1% respectively; i.e., after 30 minutes pre-conditioning, the rejection of each, pyritic sulfur, total sulfur and ash, increased by 22.7%, 21%, and 15.6%, respectively, while the pyritic sulfur, total sulfur and ash contents reduced to 0.15%, 0.66%, and 6.02% respectively. From Table 5, it is clear that the froth flotation reduced the pyritic sulfur content from 1.57% to 0.58% (about 70% rejection), while the bacterial pre-conditioning reduced it from 0.58% to 0.15% after 30 minutes; i.e., the total pyritic sulfur rejection is 93%. but after 10 minutes of bacterial pre-conditioning the pyritic sulfur content reduced to 0.27%; i.e., the total pyritic sulfur rejection is 86.7% only after 10 minutes bacterial pre-conditioning.

For Pittsburgh No. 8 Coal from FIG. 4 and Table 6, it is clear that the coal recovery is decreased by about 5.6% due to the bacterial pre-conditioning for 30 minutes. From Table 6, the ash rejection is increased by about 11.7% at the same pre-conditioning time. The pyritic sulfur rejection shown in FIG. 4 is increased by about 27.2%, while the pyritic sulfur content decreased from 1.93% to 0.45%; i.e., about 1.48% pyritic sulfur content reduction after 30 minutes bacterial treatment with 4 weeks adapted *T. ferrooxidans*. The total sulfur rejection increased by about 25.4%, while the total sulfur content decreased from 2.63% to 1.09%; i.e., about 1.54% reduction in total sulfur content after 30 minutes pre-conditioning. From Table 6, it is clear that the froth flotation with about 3.0 lb/ton flotation reagents could reduce the pyritic sulfur content from 3.8% to 1.93%, while the bacterial pre-conditioning for 30 minutes decreases it from 1.93% to 0.45%; i.e., about 92.9% of pyritic sulfur was removed due to the pre-conditioning with 4 weeks adapted bacteria followed by froth flotation with 3.0 lb/ton flotation reagents, while the bacterial pre-conditioning for only 10 minutes reduces the pyritic sulfur from 1.93% to 1.07%; i.e., about 82.1% of pyritic sulfur was removed after only 10 minutes of bacterial pre-conditioning.

For bacteria adapted for 6 weeks, FIG. 5 and Table 7 show that the coal recovery was slightly decreased by about 4% due to the bacterial pre-conditioning of Upper Freeport Coal for 30 minutes. The pyritic sulfur, total sulfur and ash rejections were increased by about 23.8%, 21.5%, and 17.8%, respectively, while the pyrite sulfur, total sulfur, and ash contents reduced to 0.13%, 0.65%, and 6% respectively after 30 minutes of bacterial pre-conditioning.

From Table 7, it is clear that the froth flotation decreased the pyritic sulfur content from 1.59% to 0.58%, while 30 minutes bacterial pre-conditioning reduced it from 0.58% to 0.15%; i.e., 93.9% total rejection, while after 10 minutes pre-conditioning, its content reduced to 0.21%; i.e., about 89.7% pyritic rejection after 10 minutes bacterial-preconditioning.

FIG. 5 and Table 8 show that the coal recovery from Pittsburgh No. 8 decreases by about 6.4% due to the bacterial pre-conditioning for 30 minutes. In addition, the ash rejection increased by about 13.5% for the same period of treatment. Pyritic sulfur rejection increased by about 28.3%, while the pyritic sulfur content decreased from 1.9% to 0.35%; i.e., about 1.54% reduction in the pyritic sulfur content after 30 minutes bacterial pre-conditioning with 6 weeks adapted *T. ferrooxidans*. Total sulfur rejection increased by about 25.9%, while the total sulfur content decreased from 2.55% to 0.99%; i.e., about 1.56% reduction in total sulfur content after 30 minutes pre-conditioning.

From Table 8, it is clear that the froth flotation with about 3.0 lb/ton flotation reagents could reduce the pyritic sulfur content from 3.8% to 1.9%, while the bacterial pre-conditioning for 30 minutes decreases it from 1.9% to 0.36%; i.e., about 94.9% of pyritic sulfur was removed due to the pre-conditioning with 6 weeks adapted cultures followed by froth flotation with 3.0 lb/ton flotation reagents, while the bacterial pre-conditioning for only 10 minutes reduces the pyritic sulfur from 1.9% to 0.85%; i.e., about 85.8% of pyritic sulfur was removed after only 10 minutes of bacterial pre-conditioning with 6 weeks adapted *T. ferrooxidans*, followed by froth flotation with 3.0 lb/ton flotation reagents.

From the previous data, it can be concluded that the adaptation period of *T. ferrooxidans* on the pyritic coal before the pre-conditioning has a significant effect on the pyritic sulfur rejection in content, especially at smaller pre-conditioning time, e.g. after 10 minutes of bacterial pre-conditioning. Ten minutes of pre-conditioning with 6 week adapted bacteria has nearly the same effect as 30 minutes of pre-conditioning with 2 week adapted bacteria. Generally it can be concluded that for the same preconditioning time, the increase of the adaptation period on the pyrite mineral before the pre-conditioning leads to more pyritic sulfur rejection and less pyritic sulfur content, but this effect of adaptation period decreases as the pre-conditioning time is increased.

The results obtained from these experiments show that conventional froth flotationn process using the flotation reagent dosages selected above can reject 60% to 70% of the pyritic sulfur from coal and also get 80% to 90% coal recovery. However, with bacterial pre-conditioning, an adaptation in accordance with the present invention the pyritic sulfur rejection is increased from 60% to 70% without bacterial treatment to 85% to 95% rejection after 30 minutes of pre-conditioning in accordance with the present invention. So by using the present invention, the coal's pyritic sulfur content could reach a very low level of 0.13% to 0.36%, depending upon the initial pyritic sulfur in the raw coal. Total sulfur content of less than 1% can be easily achieved by the present invention.

FIG. 6 and 7 illustrate the relationship between the bacterial adaptation period and the pre-conditioning time of coal.

FIG. 6 shows the influence of adaptation period of the bacteria on the pre-conditioning time required to reach a pyritic sulfur content of 0.27% and 0.2% of Upper Freeport coal. With two weeks adapted bacteria these levels of pyritic sulfur content can be achieved after 18 and 30 minutes of bacterial pre-conditioning respectively, while with six weeks adapted bacteria it needs only 5 and 12 minutes of bacterial pre-conditioning respectively to achieve the same levels of pyritic sulfur content; i.e., the increase of the adaptation period from two to six weeks leads to a decrease of the bacterial pre-conditioning time by 72% and 60%, respectively. FIG. 7 shows similar effect for Pittsburgh No. 8 coal for which the levels of 1.09% and 0.56% of pyritic sulfur can be achieved after 12 and 30 minutes of bacterial pre-conditioning respectively with two weeks adapted bacteria, while the same levels of pyritic sulfur content can be achieved in a shorter time of 5 and 20 minutes of bacterial pre-conditioning respectively with six weeks adapted bacteria; i.e., the increase of the adaptation period from two to six weeks leads to a decrease in the bacterial pre-conditioning time by 58% and 33%, respectively.

From FIGS. 6 and 7 it can be concluded that the increase of bacterial adaptation period leads to significant decrease in the bacterial pre-conditioning time required to achieve a certain level of pyritic sulfur content.

Tables 9 and 10 represent a comparison of conventional froth flotation process to 5, 10 and 30 minute pre-conditioning times using 6 week adapted bacteria.

Table 9 shows that the pyritic sulfur content of Upper Freeport coal, which is initially 1.59% is reduced to 0.58% by conventional froth flotation, but is essentially reduced again in half to 0.27% by 5 minutes of pre-conditioning and halved again to 0.13% with 30 minutes of the pre-conditioning. At the same time, the coal recovery percent is reduced only from 91.2% to 87.8%.

Similar results are shown in Table 10, where the pyritic content of Pittsburgh No. 8 is initially 3.8% which is reduced essentially in half by conventional froth flotation to 1.9%. However, it is again reduced essentially in half by 5 minutes of pre-conditioning with the 6 week adapted bacteria to 1.09% and is cut in essentially one third further to 0.36% by 30 minutes of pre-conditioning with the 6 week adapted bacteria.

TABLE 9

COMPARISON OF CONVENTIONAL FROTH FLOTATION TO
PRECONDITIONING USING 6 WEEK ADAPTED BACTERIA
UPPER FREEPORT COAL
(1.75 LBS/TON FLOTATION REAGENT)

| | CONTENT PERCENT BY WEIGHT | | | REJECTION PERCENT | | | COAL |
|---|---|---|---|---|---|---|---|
| | ASH | TOTAL SULFUR | PYRITIC SULFUR | ASH | TOTAL SULFUR | PYRITIC SULFUR | RECOVERY PERCENT |
| FEED (RAW COAL) | 18.86 | 2.1 | 1.59 | — | — | — | — |
| CONVENTIONAL FROTH FLOTATION | 9.61 | 1.15 | 0.58 | 49 | 45.2 | 63.5 | 91.2 |
| 5 MINUTES PRECONDITIONING | 8.79 | 0.81 | 0.27 | 53.3 | 61.4 | 83 | 88.5 |
| 10 MINUTES PRECONDITIONING | 7.92 | 0.75 | 0.21 | 58 | 64.3 | 86.8 | 88.7 |
| 30 MINUTES PRECONDITIONING | 6.0 | 0.69 | 0.13 | 68.2 | 0.69 | 91.8 | 87.1 |

TABLE 10

COMPARISON OF CONVENTIONAL FROTH FLOTATION TO
PRECONDITIONING USING 6 WEEK ADAPTED BACTERIA
PITTSBURGH NO. 8 COAL
(3.0 LBS/TON FLOTATION REAGENT)

| | CONTENT PERCENT BY WEIGHT | | | REJECTION PERCENT | | | COAL |
|---|---|---|---|---|---|---|---|
| | ASH | TOTAL SULFUR | PYRITIC SULFUR | ASH | TOTAL SULFUR | PYRITIC SULFUR | RECOVERY PERCENT |
| FEED (RAW COAL) | 33.78 | 4.42 | 3.8 | — | — | — | — |
| CONVENTIONAL FROTH FLOTATION | 20.6 | 2.55 | 1.9 | 39.2 | 42.3 | 50 | 81.4 |
| 5 MINUTES PRECONDITIONING | 18.86 | 1.77 | 1.09 | 44.3 | 59.95 | 71.3 | 79.7 |
| 10 MINUTES PRECONDITIONING | 17.55 | 1.48 | 0.85 | 48.2 | 66.5 | 77.6 | 79 |
| 30 MINUTES PRECONDITIONING | 15.92 | 0.99 | 0.36 | 53 | 77.6 | 90.5 | 75 |

It will be apparent to those skilled in the art that numerous changes and improvements may be made in the preferred embodiment of the invention without departing from the scope of the invention. Accordingly, the above description is to be construed in an illustrative and not in a limitative sense, the scope of the invention being defined solely by the appended claims.

We claim:

1. A method of removing pyrite from a finely ground pyrite-containing coal, comprising:
   (a) growing a culture of thiophilic bacteria in a nutrient medium,
   (b) adapting said grown culture to pyrite as a nutrient source and to coal pyrite surface modification conditions by admixing said culture with a slurry of ground coal pyrite or of ground pure pyrite from non-coal sources, under conditions favorable for bacterial growth and activity including an initial pH level below 4.0, and stirring and aerating for an adaptation time period of at least one week which is sufficient to substantially enhance the ability of the bacteria to decrease the relative hydrophobicity of pyrite particles;
   (c) preconditioning the pyrite-containing coal by admixing a slurry of it with the adapted culture and causing the resultant composition to remain in admixture under coal pyrite modification conditions for a preconditioning time period of less than substantially 100 minutes; and
   (d) subjecting said pyrite-containing coal to a coal separation process based on relative hydrophobicity.

2. A method as in claim 1, wherein after step (c), the composition is separated into a liquid portion comprising said bacteria and a solid portion comprising said pyrite-containing coal, said liquid portion is recycled for reuse as said culture in step (c), and said solid portion is re-slurried prior to being subjected to said process of step (d).

3. A method as in claim 1, wherein the adaptation of step (b) more particularly comprises admixing the grown culture with a slurry of that ground coal pyrite which is of a higher pyrite content than naturally occurs in coal and stirring and aerating the slurry mixture.

4. A method as in claim 3, wherein after step (c), the composition is separated into a liquid portion comprising said bacteria and a solid portion comprising said pyrite-containing coal, said liquid portion is recycled for reuse as said culture in step (c), and said solid portion is re-slurried prior to being subjected to said process of step (d).

5. The method as in claim 3 wherein the preconditioning of step (c) more particularly comprises admixing the adapted culture with the finely ground coal which is to be subjected to the separation process of step (d) and stirring and aerating the slurry mixture.

6. A method as in claim 5, wherein after step (c), the composition is separated into a liquid portion comprising said bacteria and a solid portion comprising said pyrite-containing coal, said liquid portion is recycled for reuse as said culture in step (c), and said solid portion is re-slurried prior to being subjected to said process of step (d).

7. A method as in claim 5, wherein the coal separation process of step (d) is a froth flotation process wherein flotation reagents are admixed with a slurry of said ground coal and the mixture is stirred and aerated whereby the hydrophobic particles are attached to ascending bubbles and collected on the top surface as a froth and the relatively hydrophillic particles settle to the bottom.

8. A method as in claim 7, wherein after step (c), the composition is separated into a liquid portion comprising said bacteria and a solid portion comprising said pyrite-containing coal, said liquid portion is recycled for reuse as said culture in step (c), and said solid portion is re-slurried prior to being subjected to said process of step (d).

9. A method as in claims 1, 2, 3, 4, 5, 6, 7 or 8, wherein said culture comprises bacteria of the species *Thiobacillus ferrooxidans*.

10. A method as in claim 1, 2, 3, 4, 5, 6, 7 or 8, wherein said coal pyrite modification conditions of steps (b) and (c) comprise an initial pH level below 4.0 and a temperature substantially in the range of 25°–35° C.

11. A method as in claim 10, wherein the initial pH is substantially in the range of 2.0 to 2.5 and the temperature is substantially 30° C.

12. A method as in claims 1, 2, 3, 4, 5, 6, 7 or 8, wherein said adaptation period is at least one week.

13. A method as in claim 12, wherein said adaptation period is at least two weeks.

14. A method as in claim 13, wherein said adaptation period is at least 6 weeks.

15. A method as in claims 1, 2, 3,, 4, 5, 6, 7 or 8, wherein said adaptation period is at least substantially one week and said preconditioning period is less than substantially 100 minutes.

16. A method as in claim 15, wherein said adaptation period is at least substantially two weeks and said preconditioning period is less than substantially 30 minutes.

17. A method as in claim 16, wherein said adaptation period is at least substantially 6 weeks and said preconditioning period is substantially in the range of 10 minutes to 20 minutes.

18. In a method for separating pyrite from pyrite-containing coal, the method being of the type wherein the coal is ground into particles to liberate the pyrite and the particles are thereafter separated on the basis of their different hydrophobicity, the improvement comprising:
   adapting active thiophillic bacteria to coal pyrite by exposing the bacteria to coal pyrite of a higher pyrite content than naturally occurs in coal under conditions which are favorable for bacterial activity and growth including an initial pH below 4.0, a temperature substantially in the range of 25°–35°, and for a period of time of at least one week which is sufficient to substantially enhance their ability to decrease the relative hydrophobicity of pyrite particles and then using the adapted bacteria to precondition the ground particles by subjecting the surfaces of the pyrite particles to the adapted thiophillic bacteria under conditions which are favorable for bacterial activity and growth for a period of time of less than substantially 100 minutes to permit the bacteria to act upon at least a substantial portion of the surface area of the pyrite before separating the pyrite from the coal.

19. A method in accordance with claim 18, wherein said adapting and said preconditioning are performed using a ground coal and water slurry which is stirred and aerated during adaptation and preconditioning.

20. A method in accordance with claim 19 wherein, after said preconditioning, the bacteria containing water is removed from the slurry and used to precondition additional ground coal particles.

21. A method in accordance with claim 20, wherein said bacteria is Thiobacillus ferrooxidans and the slurries are adjusted to an initial pH of substantially 2 to 2.5 and a temperature of substantially 20° C. to 40° C.

22. A method in accordance with claim 21, wherein said bacteria is adapted for at least substantially 2 weeks and said coal is preconditioned for less than substantially 30 minutes.

23. A method in accordance with claim 22, wherein said bacteria is adapted for at least substantially 6 weeks and said coal is preconditioned for less than substantially 5 minutes.

24. A method of removing pyrite from finely-divided pyrite-containing coal, comprising the following steps:
  (a) obtaining an inactive culture of thiophilic bacteria originally grown on a medium, comprising ferrous sulfate, and activating said culture by growing in an aqueous nutrient medium, comprising ferrous sulfate and sulfuric acid;
  (b) adapting said culture from step (a) to pyrite as a nutrient medium and to coal-pyrite surface modification conditions by slurring the bacteria of said culture from step (a) with −200 mesh pyrite, or −200 mesh coal pyrite of a pyrite content of about 60 percent, and stirring and aerating for at least six weeks at a pH level below about 4.0 and a temperature in the range of about 25°–35° C. to provide a modified adapted culture effective for subsequently reducing hydrophobicity of pyrite particles;
  (c) slurrying the adapted culture from step (b) with said finely-divided pyrite-containing coal with stirring and aerating for a time period on the order of five to fifteen minutes at a pH level below about 4.0 and a temperature in the range of about 25°–35° C. to precondition said finely-divided pyrite-containing coal by reducing hydrophobicity of pyrite particles therein;
  (d) separating the slurry composition resulting from step (c) into a solid portion comprising said pyrite-containing coal and a liquid portion comprising an adapted culture comprising bacteria;
  (e) recycling said liquid portion from step (d) into step (c) with supplementation by a minor amount of the adapted culture from step (b); and
  (f) reslurrying the solid portion from step (d) and subjecting to a coal separation process, based on hydrophobicity, of froth flotation to provide a froth containing a coal of significantly reduced pyrite content.

25. The method of claim 24 employing *Thiobacillus ferrooxidans* for said thiophilic bacteria

* * * * *